United States Patent
Montgomery et al.

[11] Patent Number: 6,162,055
[45] Date of Patent: Dec. 19, 2000

[54] LIGHT ACTIVATED TOOTH WHITENING COMPOSITION AND METHOD OF USING SAME

[75] Inventors: Robert Eric Montgomery, Monterey, Mass.; Salim A. Nathoo, Piscataway, N.J.

[73] Assignee: BriteSmile, Inc., Walnut Creek, Calif.

[21] Appl. No.: 09/234,038

[22] Filed: Jan. 19, 1999

Related U.S. Application Data

[60] Provisional application No. 60/074,708, Feb. 13, 1998, and provisional application No. 60/075,222, Feb. 19, 1998.

[51] Int. Cl.[7] .................................................. A61K 7/16
[52] U.S. Cl. ............................................. 433/216; 433/29
[58] Field of Search ............................. 433/29, 215, 216

[56] References Cited

U.S. PATENT DOCUMENTS

| | | | |
|---|---|---|---|
| Re. 34,196 | 3/1993 | Munro | 433/215 |
| 4,256,730 | 3/1981 | Benedict | 424/52 |
| 4,661,070 | 4/1987 | Friedman | 433/203.1 |
| 4,837,008 | 6/1989 | Rudy et al. | 424/53 |
| 4,971,782 | 11/1990 | Rudy et al. | 424/53 |
| 4,976,955 | 12/1990 | Libin | 424/53 |
| 4,983,380 | 1/1991 | Yarborough | 424/52 |
| 4,983,381 | 1/1991 | Zaragoza | 424/53 |
| 5,009,885 | 4/1991 | Yarborough | 424/53 |
| 5,032,178 | 7/1991 | Cornell | 106/35 |
| 5,098,303 | 3/1992 | Fischer | 433/215 |
| 5,171,564 | 12/1992 | Nathoo et al. | 424/53 |
| 5,234,342 | 8/1993 | Fischer | 433/215 |
| 5,240,415 | 8/1993 | Haynie | 433/215 |
| 5,256,402 | 10/1993 | Prencipe et al. | 424/53 |
| 5,279,816 | 1/1994 | Church et al. | 424/53 |
| 5,302,375 | 4/1994 | Viscio | 424/53 |
| 5,376,006 | 12/1994 | Fischer | 433/215 |
| 5,401,495 | 3/1995 | Murayama | 424/49 |
| 5,409,631 | 4/1995 | Fischer | 252/186.25 |
| 5,425,953 | 6/1995 | Sintov et al. | 424/404 |

(List continued on next page.)

FOREIGN PATENT DOCUMENTS

| | | |
|---|---|---|
| WO 91/14650 | 10/1991 | WIPO. |
| WO 97/11676 | 4/1997 | WIPO. |
| WO 98/04235 | 2/1998 | WIPO. |
| 98/58595 | 12/1998 | WIPO. |

OTHER PUBLICATIONS

Clinical Research Associates Newsletter, vol. 16, Issue 3, (Mar. 1992).
The Dental Advisor Plus, vol. 6 No. 1, (Jan./Feb. 1996).
C. G. Toh, "Clinical Evaluation of a dual–activated bleaching system"; Asian J. Aesthet. Dent, I: 65–70, (1993).
QuasarBrite™, Contrast A.M.®, Laser Whitening Gel, Instructions for Use Manual, Interdent, Inc. (Los Angeles, CA) (no date).
Shofu®, HiLite® Dual Activated Bleaching System, Instruction Manual, Shofu Dental Corporation (Menlo Park, CA) Nov. 1997.
Goldstein et al., eds., *Complete Dental Bleaching*, Ch. 4, Quintessence Publishing Co., Inc., Chicago (1995).
Montgomery et al., "Photoinduced Stain Removal in Bovine Enamel," *Journal of Dental Research*, 78: Abstract # 1158 (1999).
Ultradent Promotional Catalog, "Opalescence® Xtra™ Whitening Gel & OpalDam™ Reflective Resin Barrier," Ultradent Products, Inc., pp. 1–4, Utah (1998).
Union Broach Operator's Manual, "Operating Instructions Illuminator," Union Broach, A Health–Chem Company, pp. 1–15.

Primary Examiner—Ralph A. Lewis
Attorney, Agent, or Firm—Kalow & Springut LLP

[57] ABSTRACT

The present invention provides a tooth whitening composition having a transparent first component that is a carrier compound and a transparent second component that is an oxidizing compound which when applied to a stained tooth and exposed to actinic light is activated to facilitate tooth whitening. The invention also provides a method for light-activated tooth whitening which comprise applying a tooth-whitening composition to one or more teeth and exposing said composition to actinic light to activate said oxidizing compound.

12 Claims, 8 Drawing Sheets

U.S. PATENT DOCUMENTS

| | | | |
|---|---|---|---|
| 5,531,915 | 7/1996 | Perkins | 510/294 |
| 5,599,525 | 2/1997 | Hsu et al. | 424/49 |
| 5,645,428 | 7/1997 | Yarborough | 433/215 |
| 5,676,933 | 10/1997 | Hauschild | 424/53 |
| 5,690,913 | 11/1997 | Hsu et al. | 424/53 |
| 5,713,738 | 2/1998 | Yarborough | 433/215 |
| 5,718,886 | 2/1998 | Pellico | 424/53 |
| 5,725,843 | 3/1998 | Fischer | 424/49 |
| 5,746,598 | 5/1998 | Fischer | 433/216 |
| 5,766,011 | 6/1998 | Sibner | 433/215 |
| 5,770,105 | 6/1998 | Fischer | 252/186.25 |
| 5,770,182 | 6/1998 | Fischer | 424/49 |
| 5,785,527 | 7/1998 | Jensen et al. | 433/215 |
| 5,816,802 | 10/1998 | Montgomery | 433/80 |
| 5,858,332 | 1/1999 | Jensen et al. | 424/53 |

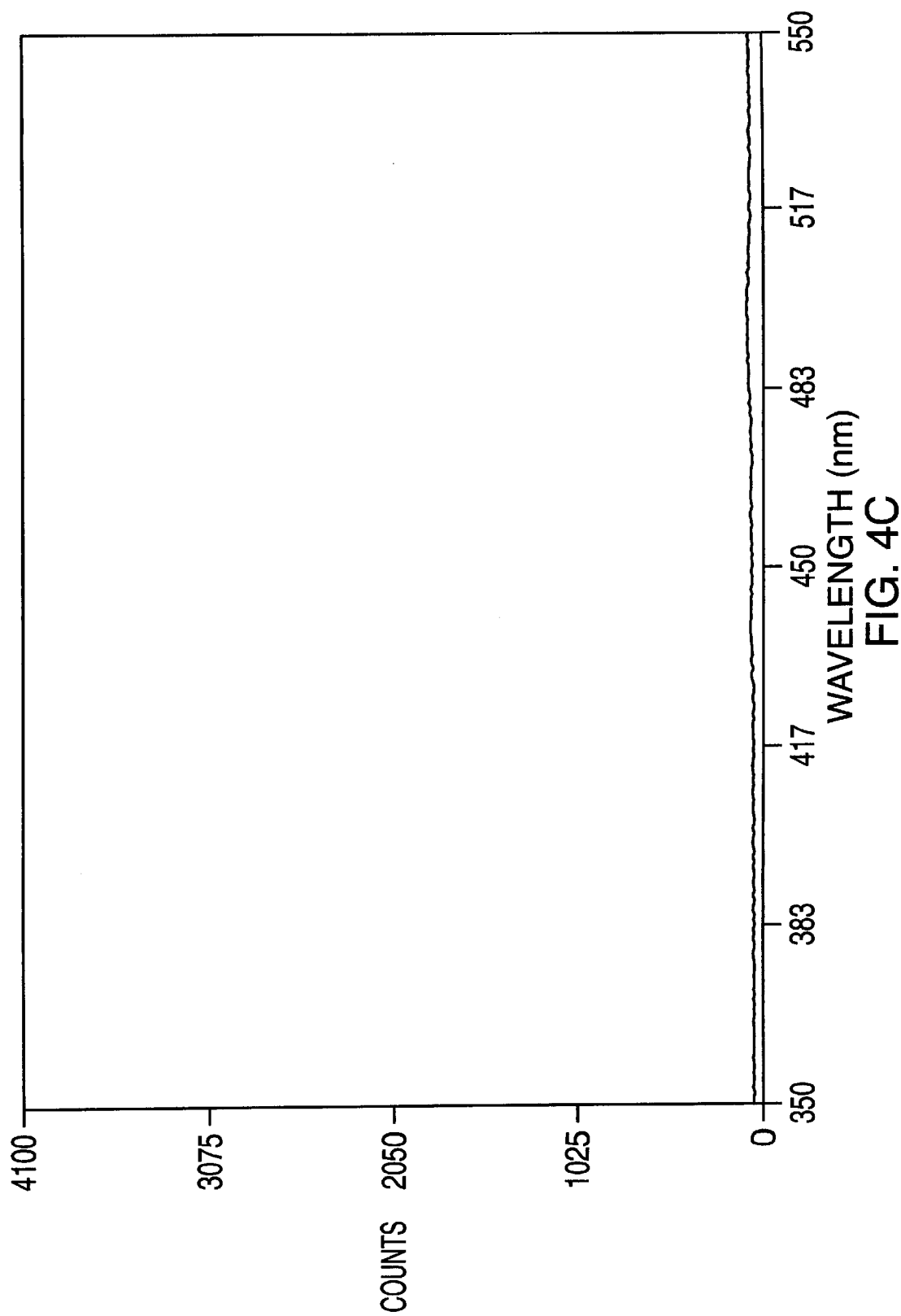

LIGHT ACTIVATED TOOTH WHITENING COMPOSITION AND METHOD OF USING SAME

The present application claims priority from provisional application Ser. No. 60/074,708, filed Feb. 13, 1998 and Ser. No. 60/075,222, filed Feb. 19, 1998, the contents of which are hereby incorporated by reference into the present disclosure.

BACKGROUND OF THE INVENTION

This invention relates to improvements in tooth whitening compositions and methods of using same. In particular, the invention provides novel tooth whitening compositions and methods that use light energy to achieve a faster and improved level of tooth whitening.

White teeth have long been considered cosmetically desirable. Unfortunately, due to the presence of chromogenic (color-causing) substances in food, beverages, tobacco, and salivary fluid, in addition to internal sources such as blood, amalgam restoratives, and antibiotics such as tetracycline, teeth become almost invariably discolored in the absence of intervention. The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer on the surface of tooth enamel which reforms rapidly after an intensive tooth cleaning.

A tooth stain classification system, termed the N (Nathoo) Classification System, has been proposed (J. of the Amer. Dental Asso., Vol. 128, Special Supplement, April 1997). One form of direct dental stain is the N1 type stain which occurs when a chromogenic material binds to the tooth surface to cause discoloration similar in color to that of the unbound chromogen. Another type of direct dental stain is the N2 type stain, in which a chromogenic material binds to the toothsurface and subsequently undergoes a color change after binding to the tooth. Finally, an N3 stain is an indirect dental stain, caused by the binding of a colorless material (prechromogen) to the tooth, said prechromogen undergoing a chemical reaction that converts it into a chromogen that causes tooth stain. Tooth stains may be either extrinsic or intrinsic, depending upon their location within the tooth structure. For example, extrinsic staining of the acquired pellicle arises as a result of compounds such as tannins and other polyphenolic compounds which become trapped in and tightly bound to the proteinaceous layer on the surface of the teeth. This type of staining can usually be removed by mechanical methods of tooth cleaning that remove all or part of the acquired pellicle together with the associated stain. In contrast, intrinsic staining occurs when chromogens or prechromogens penetrate the enamel and dentin and become tightly bound to the tooth structure. Intrinsic staining may also arise from systemic sources of chromogens or prechromogens, for instance, when excess fluoride intake during enamel development leads to the mottled yellow or brown spots typical of fluorosis staining. Intrinsic staining is not amenable to mechanical methods of tooth cleaning and generally requires the use of chemicals, such as hydrogen peroxide, that can penetrate into the tooth structure, in order to affect a change in the light absorptivity of the chromogen. Intrinsic tooth staining is generally more intractable and difficult to remove than extrinsic tooth staining.

Consequently, tooth-bleaching compositions generally fall into two categories: (1) gels, pastes, or liquids, including toothpastes that are mechanically agitated at the stained tooth surface in order to affect tooth stain removal through abrasive erosion of stained acquired pellicle; and (2) gels, pastes, or liquids that accomplish the tooth-bleaching effect by a chemical process while in contact with the stained tooth surface for a specified period, after which the formulation is removed. In some cases, an auxiliary chemical process or additive, which may be oxidative or enzymatic, supplements the mechanical process.

Among the chemical strategies available for removing or destroying tooth stains, the most effective compositions contain an oxidizing agent, such as hydrogen peroxide, in order to attack the chromogen molecules in such a way as to render them colorless, water-soluble, or both. In one of the most popular approaches to whitening a patient's teeth, a dental professional will construct a custom-made tooth-bleaching tray for the patient from an impression made of the patient's dentition and prescribe the use of an oxidizing gel to be dispensed into the tooth-bleaching tray and worn intermittently over a period of time ranging from about 2 weeks to about 6 months, depending upon the severity of tooth staining. These oxidizing compositions, usually packaged in small plastic syringes, are dispensed directly by the patient, into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition. The most commonly used oxidative compositions contain the hydrogen peroxide precursor carbamide peroxide which is mixed with an anhydrous or low-water content, hygroscopic viscous carrier containing glycerin and/or propylene glycol and/or polyethylene glycol. When contacted by water, carbamide peroxide dissociates into urea and hydrogen peroxide. Associated with the slow rate of bleaching in the hygroscopic carrier, the currently available tooth-bleaching compositions cause tooth sensitization in over 50% of patients. Tooth sensitivity is believed to result from the movement of fluid through the dentinal tubules, which is sensed by nerve endings in the tooth. The carriers for the carbamide peroxide enhance this movement. In fact, it has been determined that glycerin, propylene glycol and polyethylene glycol can each give rise to varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These include: solubilization of calcium from the enamel layer at a pH less than 5.5 with associated demineralization; penetration of the intact enamel and dentin by the bleaching agents, so as to reach the pulp chamber of a vital tooth thereby risking damage to pulpal tissue; and dilution of the bleaching compositions with saliva resulting in leaching from the dental tray and subsequent ingestion.

Alternatively, there are oxidizing compositions (generally those with relatively high concentrations of oxidizers) which are applied directly to the tooth surface of a patient in a dental office setting under the supervision of a dentist or dental hygienist. Theoretically, such tooth whitening strategies have the advantage of yielding faster results and better overall patient satisfaction; however, due to the high concentration of oxidizing agents contained in these so called "in-office" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), through which only the teeth protrude. Alternatively, the soft tissue may be isolated from the oxidizers to be used in the whitening process by covering said soft tissue with a polymerizable composition that is shaped to conform to the gingival contours and subsequently cured by exposure to a high intensity light source. Once the soft tissue has been isolated and protected, the practitioner may apply the oxidizing agent directly onto the stained tooth surfaces for a specified period of time or until a sufficient change in tooth color has occurred. Typical results obtained through the use of a in-office tooth whitener, with or without activation by heat, range from about 2 to 3 shades (as measured with the VITA® Shade Guide, VITA® Zahnfarbik, Bad Sackingen, Germany).

The range of tooth shades in the VITA® Shade Guide varies from very light (B 1) to very dark (C4). A total of 16 tooth shades constitute the entire range of colors between these two endpoints on a scale of brightness. Patient satisfaction with a tooth whitening procedure increases with the number of tooth shade changes achieved. Typically, the minimum generally accepted change is about 4 to 5 VITA® shades.

Attempts have been made to activate peroxides with heat and/or light for the purpose of whitening teeth. U.S. Pat. No. 4,661,070 discloses a method of whitening stained teeth which includes the application of a concentrated solution of hydrogen peroxide within the pulp chamber or upon the surface of a discolored tooth, followed by exposing the discolored tooth to optical energy consisting of both ultraviolet and infrared light. The preferred wavelengths of light disclosed by this patent are from 320 to 420 nanometers and from 700 to 1200 nanometers, with light in the visible spectrum (wavelengths from 500 and 700 nanometers) being suppressed. The disclosed method suffers from two serious drawbacks: (1) ultraviolet light can be hazardous to the patient and practitioner alike and (2) infrared light may cause irreversible pulpitis if not handled with care.

These drawbacks are partially addressed in U.S. Pat. No. 4,952,143 which discloses a dental bleaching instrument which filters out ultraviolet light and has a temperature regulation mechanism. This patent also discloses the use of visible light with wavelengths ranging from 450 to 500 and 650 to 750 nanometers to produce a dark reddish/purple beam which facilitates the aiming and focusing of the instrument.

U.S. Pat. No. 5,032,178 discloses compositions and methods to improved tooth whitening efficacy which uses exposure to "optical energy", preferably in the visible spectrum wavelength range of 400 to 700 nanometers. The compositions disclosed in this patent require the use of (1) an inert silica gelling agent, (2) a catalytic accelerator (either manganese sulfate monohydrate or ferrous sulfate), (3) an agent for providing thixoplasticity and thickening properties to the composition, such as cellulose ethers and methyl vinyl ethers, and (4) a means for indicating completion of the bleaching treatment of the teeth, comprising a redox color indicator for transforming from one color to another in response to the dissociation of hydrogen peroxide over a given time period. Compositions described therein are mixed homogeneously prior to use and all of the required components, including the catalyst, are dispersed evenly throughout the mixture. The compositions described are not highly transparent to light energy in the range of 400 to 700 nm, due to the presence of the high levels of inorganic silica particles. Commercial mixtures based on this patent (available under the trade name Shofu Hi-Lite® from Shofu Dental Corporation, Menlo Park, Calif.) confirm that these preparations are not transparent to visible light, but rather are quite opaque. Typical results obtained using such compositions and methods are about 2 to 3 VITA® shades improvement in tooth color, similar to that achieved with compositions that do not employ light energy in the process of bleaching teeth.

U.S. Pat. No. 5,240,415 discloses a dental bleaching system comprising a multi-component kit, one of the required components of said kit being fumed silica. As described above, silica renders an aqueous composition relatively opaque to visible light energy. Again, a tooth shade improvement of about 2 to 3 VITA® shades can be expected through the use of this type of composition.

A commercial product called Opalescence Xtra available for bleaching teeth in the controlled environment of a dental office has recently been introduced by Ultradent Products, Inc, South Jordan, Utah. This product is believed to be based on the disclosure of U.S. Pat. No. 5,785,527. The commercial product is supplied in a plastic syringe and is described in the accompanying literature as a light-activated tooth whitening gel, which contains approximately 35% hydrogen peroxide. A pH determination showed the product to have a neat pH at 25° C. of about 4.0. The product is thickened to a loose, gel-like consistency with a polymer. Additionally, the product as sold, and as disclosed in U.S. Pat. No. 5,785,527, contains a bright orange pigment or dye (carotene), which presumably serves as the "photosensitizer". The manufacturer also claims that the photosensitizer is able to absorb light energy and convert it into heat energy, thereby increasing the activity of the peroxide as a tooth bleaching agent. The presence of a photoabsorber in the aforementioned composition renders it relatively opaque to wavelengths from about 400 to 700 nm. Exposure of this composition to light energy between 400 and 700 nm results in a gradual fading of the orange color, presumably due to a photobleaching effect in the presence of the hydrogen peroxide. Comparative clinical results show an improvement in tooth color of from about 3 to 4 VITA® shades, which is highly dependent upon the contact time of the composition on the tooth surface, rather than any particular light or heat activation regimen. In addition, the low pH of the commercial product may cause a reduction in the microhardness of tooth enamel, due to the dissolution of hydroxyapatite crystals (which can occur at a pH of around 5.5 or less).

Devices for use in light/heat-activated tooth whitening procedures include the commercially available Union Broach Illuminator System, from Union Broach, a Health\Chem Company, New York, N.Y. This device, as described by the manufacturer, provides direct, full spectrum illumination to all of the teeth found in the front of the average adult's mouth. However, this device does not uniformly illuminate all sixteen central teeth in the front upper and lower arches because of the curvature of the dentition. This potentially gives rise to uneven results. In addition, the Union Broach device generates a great deal of heat which is both uncomfortable for the patient and potentially damaging to the teeth.

There is thus a need for improved compositions, methods and devices for whitening teeth that overcome the limitations of the prior art described above. In particular, there is a need for tooth whitening compositions and methods capable of whitening teeth quickly and safely, without harm to tooth enamel, dentin, or pulp. The compositions and methods of the present invention described herein satisfy these and other needs.

It is an object of this invention to provide fast and safe tooth whitening compositions and methods that can be activated or accelerated by the use of light energy.

It is a further object of this invention to provide a tooth whitening composition that shortens the treatment time required to obtain a given level of tooth whitening that is satisfactory to both the patient and the dentist.

It is another object of the present invention to provide tooth whitening compositions that are relatively transparent to light energy in the wavelength range at which tooth chromogens absorb in order to allow exposure of the tooth enamel surface to said light energy while in contact with said tooth whitening compositions.

It is yet another object of this invention to provide compositions and methods for whitening teeth whereby the extent of tooth whitening, in addition to the types of tooth stains removed, can be controlled by the duration, intensity and wavelength of actinic radiation exposure at the tooth surface.

SUMMARY OF THE INVENTION

The present invention encompasses methods for whitening teeth, wherein a stained tooth surface is contacted with (i) a tooth whitening composition that is transparent to photoactive light and (ii) a photosensitive agent that is responsive to the wavelengths of light that are transmitted through the whitening composition and, after contacting with the composition and agent, the tooth is exposed to a biologically safe and effective level of photoactinic light in order to enhance the ability of the oxidizing compound in the whitening composition to effect rapid tooth whitening.

Also disclosed and contemplated within the scope of this invention are methods for whitening teeth, wherein a stained tooth surface is contacted with an oxidizing compound that is transparent to the wavelengths of light that are absorbed by tooth stain chromogens, and then exposing the treated tooth to a biologically safe and effective level of those same wavelengths of light in order to effect rapid tooth whitening.

Also disclosed and contemplated within the scope of this invention are the compositions and compounds described above and devices for whitening teeth, wherein a minimum of eight central teeth in both the upper and lower arches in an adult are simultaneously and uniformly illuminated with a biologically safe and effective level of actinic light to effect rapid tooth whitening.

DETAILED DESCRIPTION OF THE PREFERRED EMBODIMENTS

Figure 1:
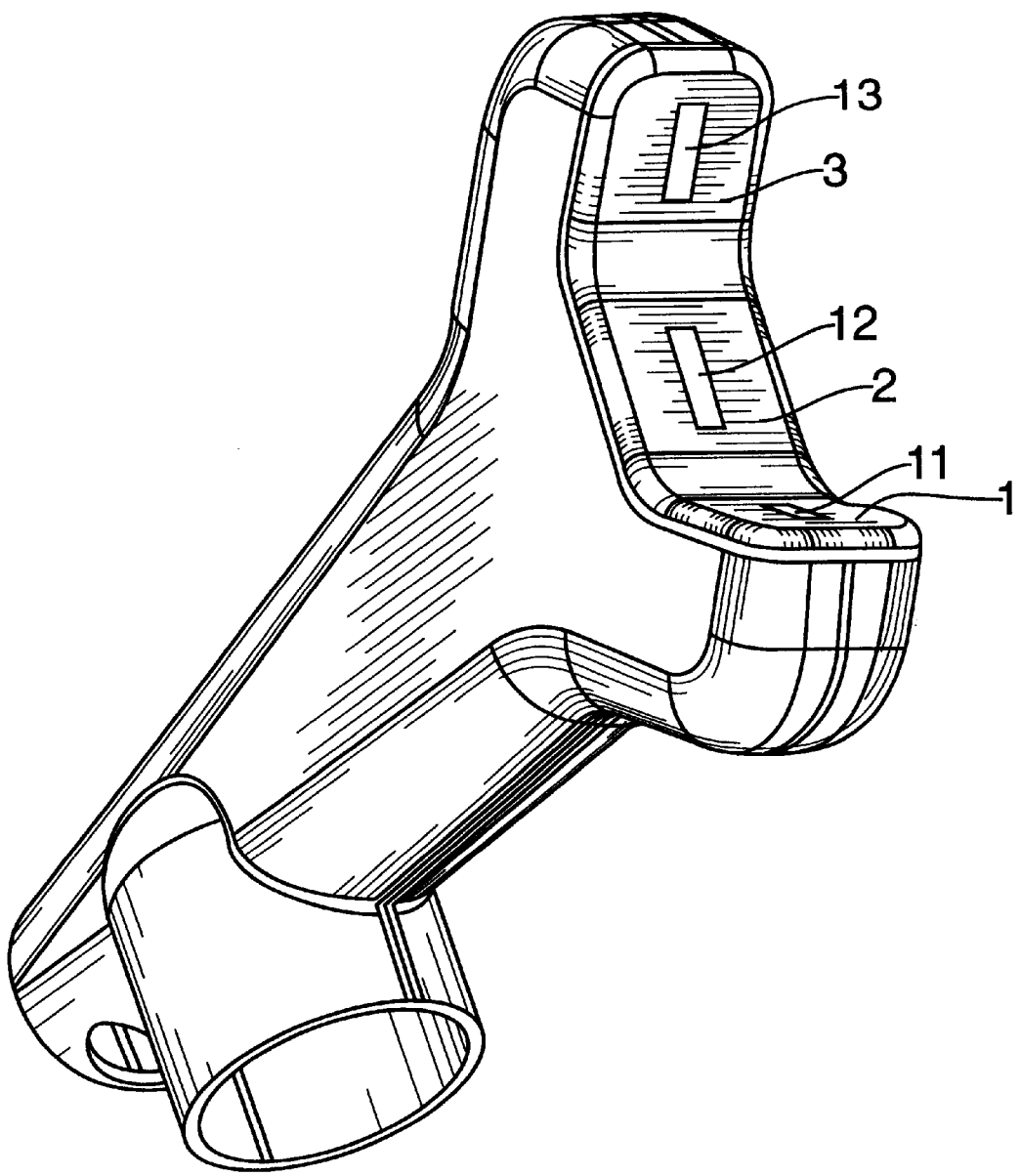
FIG. 1: A diagram of a device for illuminating the eight central teeth in both the upper and lower arches of an adult for use in a light-activated tooth whitening procedure.

This section details the preferred embodiments of the subject invention. These embodiments are set forth to illustrate the invention, but are not to be construed as limiting. Since the present disclosure is directed to those skilled in the art field and is not primer on the manufacture of tooth whitening compositions or their use or on devices for using such compositions, basic concepts and standard features known to those skilled in the art are not set forth in detail. Details for concepts such as choosing appropriate construction materials or ingredients, operating conditions or manufacturing techniques, etc. are known or readily determinable to those skilled in the art. Attention is directed to the appropriate texts and references known to those skilled in the art for details regarding these and other concepts which may be required in the practice of the invention; see, for example, Kirk-Othmer Encyclopedia of Chemical Technology, 4th Edition, Volumes 4 (1992), 13 (1995), 18 (1996), John Wiley & Sons, NY; Goldstein and Garber, *Complete Dental Bleaching,* Quintessence Publishing Co. 1995; and the aforementioned Journal of the American Dental Association, Vol. 128, Special Supplement, April 1997, the disclosures of which are hereby incorporated by reference into the present disclosure to aid in the practice of the invention. The development of the inventive compositions and methods described herein resulted from the unexpected discovery that extremely rapid tooth whitening occurs by allowing actinic radiation to penetrate through the oxidizing compound, which is placed directly onto the tooth surface to be whitened. This discovery is antithetical to all prior art compositions that include a light (or heat) absorbing additive dispersed directly in and homogeneously throughout the oxidizing compound. The inventive compositions, on the other hand, allow actinic radiation to reach the stained tooth surface at higher power densities than prior art compositions that are specifically designed to absorb light. Actinic radiation is thus more effectively utilized compared to prior art compositions and methods in which compositions are both opaque to most wavelengths of light and are activated directly by the actinic radiation. As the greatest oxidizing activity is required in the few millimeters of enamel and dentin at the tooth surface, the present inventive compositions and methods are more effective at removing tooth stains, in many cases with lower levels of active oxidizing agents, thereby resulting in safer compositions for use in the oral cavity.

For the purpose of this disclosure, the term actinic radiation shall mean light energy capable of being absorbed by either an exogenous photosensitizing agent or an indigenous tooth chromogen. Also for the purpose of this disclosure, photosensitizing actinic radiation will mean light absorbed by a specific photosensitive agent, where as chromosensitizing actinic radiation will mean light absorbed by one or more tooth chromogens. The terms "actinic radiation" and "actinic light" will be referred to interchangeably.

Also for the purposes of this disclosure, the term "transparent" shall mean having greater than 70% transmission of light at a specified wavelength or within a wavelength range. In addition, all composition ingredient percentages are by weight unless otherwise stated.

Various modes of application of the inventive tooth bleaching compositions are effective, although methods that allow for the accumulation or concentration of the photosensitizer within the acquired pellicle, enamel, and dentin (the three tooth structure primarily associated with the majority of tooth staining) are most preferred. This is best accomplished by contacting the stained tooth surface with the photosensitizer prior to contacting the same stained tooth surface with the oxidizing composition. In this way, the photosensitizer is able to penetrate into the tooth structure, thus being present at the site of the tooth chromogen(s) prior to contact with the oxidizing composition and prior to exposure to the actinic radiation source.

Photosensitizing agents useful in accomplishing the desired tooth whitening effect include any compounds capable of absorbing light energy at biologically acceptable wavelengths prescribed by the limits of safety for use in the oral cavity. In general, such wavelengths are from about 350 nanometers (nm) to about 700 nm, encompassing a portion of the UVA spectrum (300 to 400 nm) and most of the visible light spectrum (400 to 700 nm). Examples of compounds which may convert light energy to either heat of chemical energy, include semiconductor particles (particularly nanometer-scale titanium dioxide and zinc oxide), benzophenone derivatives, benzotriazole derivatives, diketones (such as camphorquinone and benzil), metal-ligand complexes (such as ferric potassium oxalate, manganese gluconate, and various metal-bisphosphonate chelates), phthalocyanin-metal complexes, and others. A specific example of a suitable photosensitizing composition is an aqueous dispersion of zinc oxide with particle sizes between 5 and 20 nanometers. Any molecule capable of absorbing a photon of light in the wavelength range of from about 350 nm to about 700 nm and subsequently converting the energy in said photon of light into the useful energy of oxidation either alone or in the presence of an auxilliary oxidizing agent, is contemplated to have utility in the practice of the present invention.

It is preferred that the inventive photosensitizers are of a molecular size, charge, pH and hydrophobicity/hydrophilicity to allow for effective penetration into the deeper structures of enamel and dentin. The more readily a photosensitizer penetrates the tooth structure, the more likely that, upon exposure of the photosensitizer to actinic radiation at the appropriate wavelength and energy, said energy will be converted into oxidative activity at the site of, or in close proximity to, the chromogen itself. Photosensitizers having a molecular size, net charge, pH, and/or a hydrophobicity/hydrophilicity which prevent or limit penetration into deeper tooth structures are of utility in the practice of the present invention, but may be limited to the removal and/or destruction of chromogens located at the outer tooth surface (extrinsic stains).

Especially preferred photosensitizers belong to the general class of water-soluble metal-ligand complexes which absorb light in the range of from about 350 nm to about 700 nm. For the purposes of the present disclosure, the term "ligand" will mean an organic molecule capable of complexing or associating with a metal ion in aqueous solution, such that the reactivity, solubility, or any other physical property of said metal ion is changed. Such metal-ligand complexes are also known as metal-coordination complexes. Suitable metals ions include iron, manganese, copper, and other transition metal ions. Various valence states may be used or may be present simultaneously. The metal ions may be present in saliva, plaque, or the acquired pellicle on the tooth surface. Metal ions may also contribute, through formation of oxides, to certain types of tooth stains. Suitable metal ion ligands include chelating agents capable of associating with the metal ions above in aqueous solution, resulting in a water-soluble metal-chelate complex that absorbs light between about 350 and 700 nm. Illustrative, but by no means limiting, examples of metal-coordination complexes are formed from the association of iron, manganese and copper with chelators such as ethylenediamine tetraacetic acid (EDTA), diethylenetriamine pentaacetic acid (DETPA), nitrilotriacetic acid (NTA), 1-hydroxyethylidene-1,1-diphosphonic acid, ethylenediamine tetra (methylenephosphonic acid), diethylenetriamine penta (methylenephosphonic acid), and polyols such as sorbitol, xylitol, mannitol, maltitol, lactitol and other non-carboxylated polyhydroxy compounds more fully described in EP 443,651, such description being incorporated herein by reference. Any organic multidentate chelating agent capable of forming a photoabsorbing coordination complex with a metal ion can be presumed to have utility in the present inventive compositions for and methods of whitening stained teeth.

A number of the inventive metal-ligand complexes have an absorption spectrum that is pH-dependent; in general, such complexes will display a greater degree of absorption between 350 and 700 nm at a pH of greater than about 4.0, light absorption in this range increasing with increasing pH. For instance, the aqueous complex formed between 1-hydroxyethylidene-1,1-diphosphonic acid and ferrous ions is virtually transparent to visible light at pH 3.0, but absorbs strongly in the spectral region between 350 and 500 nm as the pH is raised to 7.0.

In some cases, a photosensitizer precursor may be included directly within the oxidizing composition, where it does not readily absorb light in the visible region of the spectrum from 400 to 700 nm. However, upon contact with the tooth surface (when placed there with the oxidizing composition), the photosensitizer precursor may combine, for instance, with a metal ion such as iron present in saliva or found in the interstitial fluid of enamel and dentin, resulting in the formation, in situ, of an active photosensitizer capable of activating the oxidizing compound upon exposure to actinic radiation. Obviously, only those compounds that are stable in a highly oxidative environment are suitable for inclusion directly in the oxidizing composition. An example of such a compound is 1-hydroxyethylidene-1, 1-diphosphonic acid (available commercially under the trade name Dequest 2010 and sold as a 60% active solution by Monsanto Corporation, St. Louis, Mo.).

The ability of certain metal chelates to act as photosensitizers has been noted in the literature by various workers. For example, Van der Zee, et al ("Hydroxyl Radical Generation by a Light-Dependent Fenton Reaction" in Free Radical Biology & Medicine, Vol. 14, pp 105–113, 1993) described the light-mediated conversion of Fe (III) to Fe (II) in the presence of a chelating agent and hydrogen peroxide. The reduction of Fe (III) chelates by light at 300 nanometers to yield Fe (II) was shown to proceed steadily over a period of about 30 minutes, with conversions to Fe (II) ranging from about 40% to about 80%, depending upon the particular chelating compound studied. The Fe (II) thus created initiated a Fenton-type degradation of the hydrogen peroxide, yielding hydroxyl radicals that were spin-trapped and detected by electron spin resonance (ESR). It was not suggested or implied by the authors that this photochemical reaction would have utility in the oxidation of chromophores, such as those found in a human tooth.

Useful oxidizing compounds include liquids and gels, preferably containing a peroxide or peroxyacid known in the art. Such oxidizing compounds include, but are not limited to, hydrogen peroxide, carbamide peroxide, alkali metal peroxides, alkali metal percarbonates, and alkali metal perborates. Often, it may be desirable to utilize a peroxyacid compound, such as peroxyacetic acid (for instance, when attempting to eliminate highly intractable tooth stains caused by tetracycline) in the tooth whitening composition. The peroxyacid may be included directly within the oxidizing composition (providing that transparency to light energy between about 350 and about 700 nanometers is maintained). Alternatively, the peroxyacid may be formed by combining two or more separate phases (one of which contains a peroxyacid precursor, such as glyceryl triacetate and a second that contains one of the oxidizing compounds listed above) prior to application to the tooth surface. Preferably, the peroxyacid is formed in situ, by contacting the tooth surface with a peroxyacid precursor prior to the application of an oxidizing compound; the peroxyacid is thus formed only on and within the stained tooth structure, where it is most beneficial to the tooth whitening process. Suitable peroxyacid precursors include, but are not limited to, glyceryl triacetate, acetylated amino acids, acetylsalicylic acid, and N,N,N',N'-tetraacetyl ethylenediamine, vinyl acetate polymers and copolymers, acetylcholine, and other biologically acceptable acetylated compounds.

The oxidizing compounds are liquid, gel, or solid compositions transparent to the wavelength(s) of light capable of activating the photosensitizing agent at the tooth surface; light energy otherwise will be attenuated by the film or layer of oxidizing compound between the actinic radiation source and the photosensitizer at the tooth enamel surface. As the tooth enamel surface is the location of the tooth discoloration, the most effective method of whitening teeth will occur when most or all of the light energy reaches the photosensitizer at the tooth enamel surface. An example of a suitable composition that is transparent to light energy between 380 and 500 nm is a 6% hydrogen peroxide gel with a pH of about 7.0 that has been thickened to approximately 100,000 cps with neutralized carboxypolymethylene.

Another unexpected benefit of utilizing an oxidizing composition transparent to photosensitizing actinic radiation is that certain wavelengths of light seem to be absorbed by tooth chromogens in a manner that promotes their oxidation to a non-chromogenic state. Reflectance studies show that dentin and enamel transmit green light, reflect yellow/red light and absorb blue light. Although not wishing to be bound by any particular theory, light is absorbed by the molecules responsible for tooth discoloration; thus, tooth chromogens may act in a manner similar to that of photosensitizers. In particular, exposure to certain wavelengths may raise the energy state level of pi electrons carbonyl (C=O), double bond (C=C) and conjugated double bond (C=C—C=C) moieties, making them more susceptible to attack by active oxidizing species such as perhydroxyl anion (HOO—), peroxyacid anions (RCOOO—), and radical species such as hydroxyl radical (HO*) and perhydroxyl radical (HOO*). In order to destroy or solubilize chromogenic substances, the activation energy of the reaction between one of the above light-absorbing moieties and an active oxidizing species must be overcome; thus, light assisted chromogen attack leads to more efficient destruction of the molecular moieties responsible for the appearance of tooth discoloration by raising the energy state of electrons in specific chemical bonds within a light-absorbing molecule from a normal pi bonding orbital to a pi antibonding orbital. Whilst in the less stable pi antibonding orbital, a light absorbing double bond has considerable single bond character and is much more easily attacked by oxidizing agents such as peroxides and peroxyacids. In theory, actinic light of a specific energy and wavelength, simply through the process described above, may utilize a tooth chromogen molecule as a photosensitizer in order to improve the efficacy of a given oxidative composition in contact with said tooth chromogen.

A light-activated tooth whitening method, in accordance with a specific embodiment of the invention includes contacting the tooth enamel surface with the photosensitizing agent, then contacting the photosensitizer-treated tooth surface with the oxidizing compound, and, thereafter, exposing the tooth surface to light energy capable of activating the photosensitizer which, in turn, activates the oxidizing compounds at the tooth enamel surface.

Another light-activated tooth whitening method, in accordance with another embodiment of the invention includes contacting the tooth enamel surface with an oxidizing compound which contains a photosensitizer precursor, whereby said precursor is seen to absorb actinic radiation in the range of 350 to 700 nm only after contact with said tooth surface. Once the photosensitizer precursor becomes light absorbent, the tooth surface is exposed to light energy capable of activating the now absorbent photosensitizer, which in turn activates the oxidizing compound at the tooth surface to whiten the tooth.

A further light-activated tooth whitening method, in accordance with another embodiment of the invention includes contacting the tooth enamel surface with an oxidizing compound and thereafter exposing said tooth enamel surface to actinic radiation corresponding to a tooth chromogen molecule absorption wavelength. The preferred wavelengths of light in this embodiment include those between about 350 and about 700 nanometers, a more preferred embodiment include those between about 380 and about 550 nanometers with the most preferred wavelengths being between about 400 and about 505 nanometers. As in all of the methods described above, the oxidizing composition must be transparent to the actinic radiation utilized in order to allow the wavelength-specific light energy to reach the tooth surface and underlying structure.

Yet another light-activated tooth whitening method, in accordance with another embodiment of the invention includes contacting the tooth enamel surface with a peroxyacid precursor prior to contacting said tooth enamel surface with an oxidizing compound and subsequently exposing to actinic radiation as described above. The peroxyacid precursor may be placed on the tooth surface together with or separately from a photosensitizer.

Stained teeth may be treated individually, for instance, by directing the light to a single tooth surface by means of a fiber optic light guide. In this manner, several stained teeth are exposed to light in sequence, the dentist or hygienist moving the light guide from tooth to tooth during the procedure. This process is both labor intensive and time consuming for the dentist or hygienist as well as tedious for the patient. Alternatively, all of the stained teeth may be exposed to light simultaneously either by direct illumination from a light source shaped substantially like the dental arch or by indirect illumination from a light guide or device that is capable of illuminating all of the front teeth at once.

One such device for the simultaneous and uniform illumination of at least eight central teeth in both the upper and lower arches is illustrated in FIG. 1. This preferred embodiment has three linear optical outputs 11, 12, and 13 precisely positioned on three front (patient facing) surfaces 1, 2, and 3. In a more preferred six bar embodiment, two three bar devices are stacked one on the other resulting in six optical outputs on the front patient facing surfaces as illustrated in FIG. 2.

Figure 2:
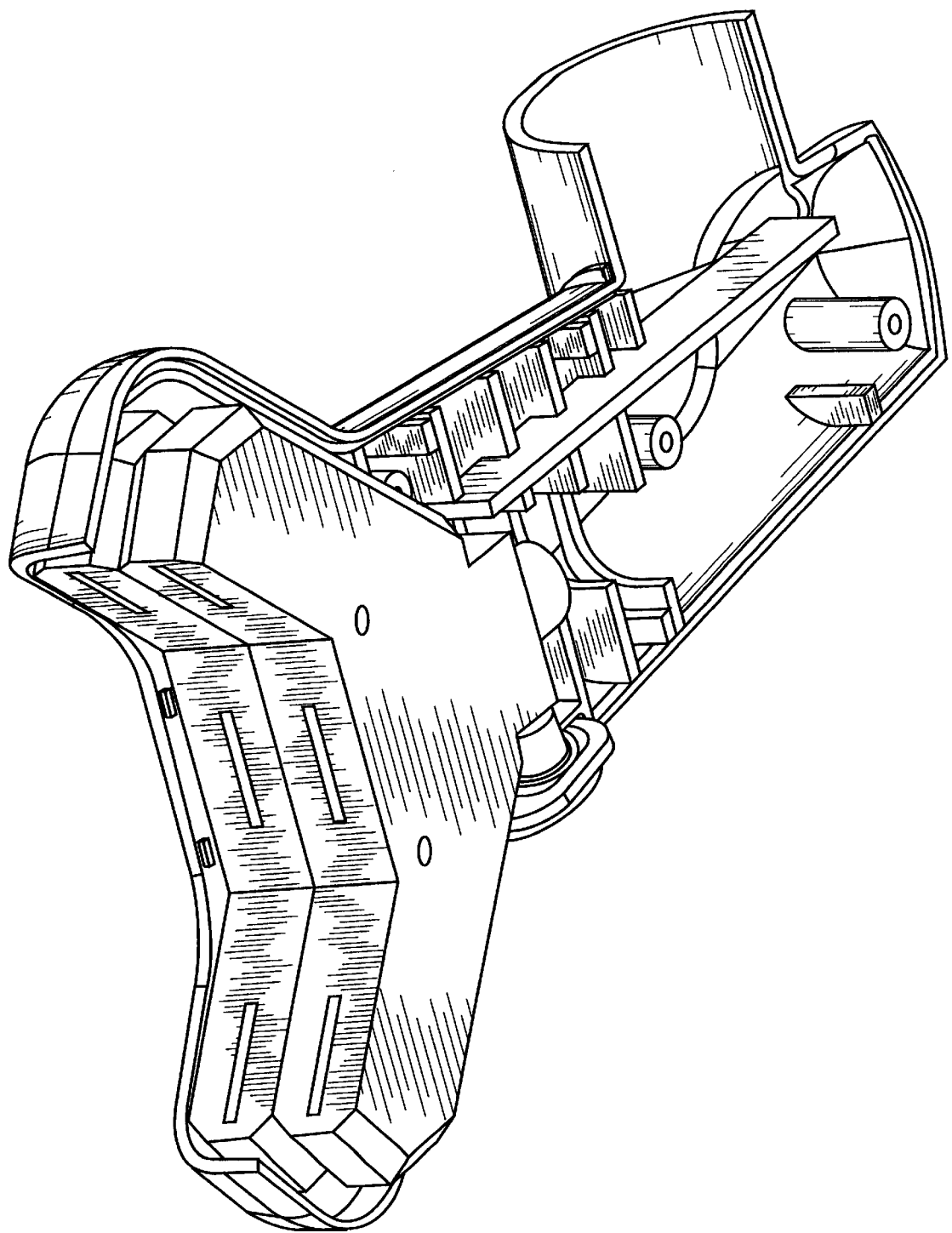
FIG. 2: A diagram illustrating the position of two devices for illuminating the eight central teeth in both the upper and lower arches of an adult for use in a light-activated tooth whitening procedure.
Figure 3:
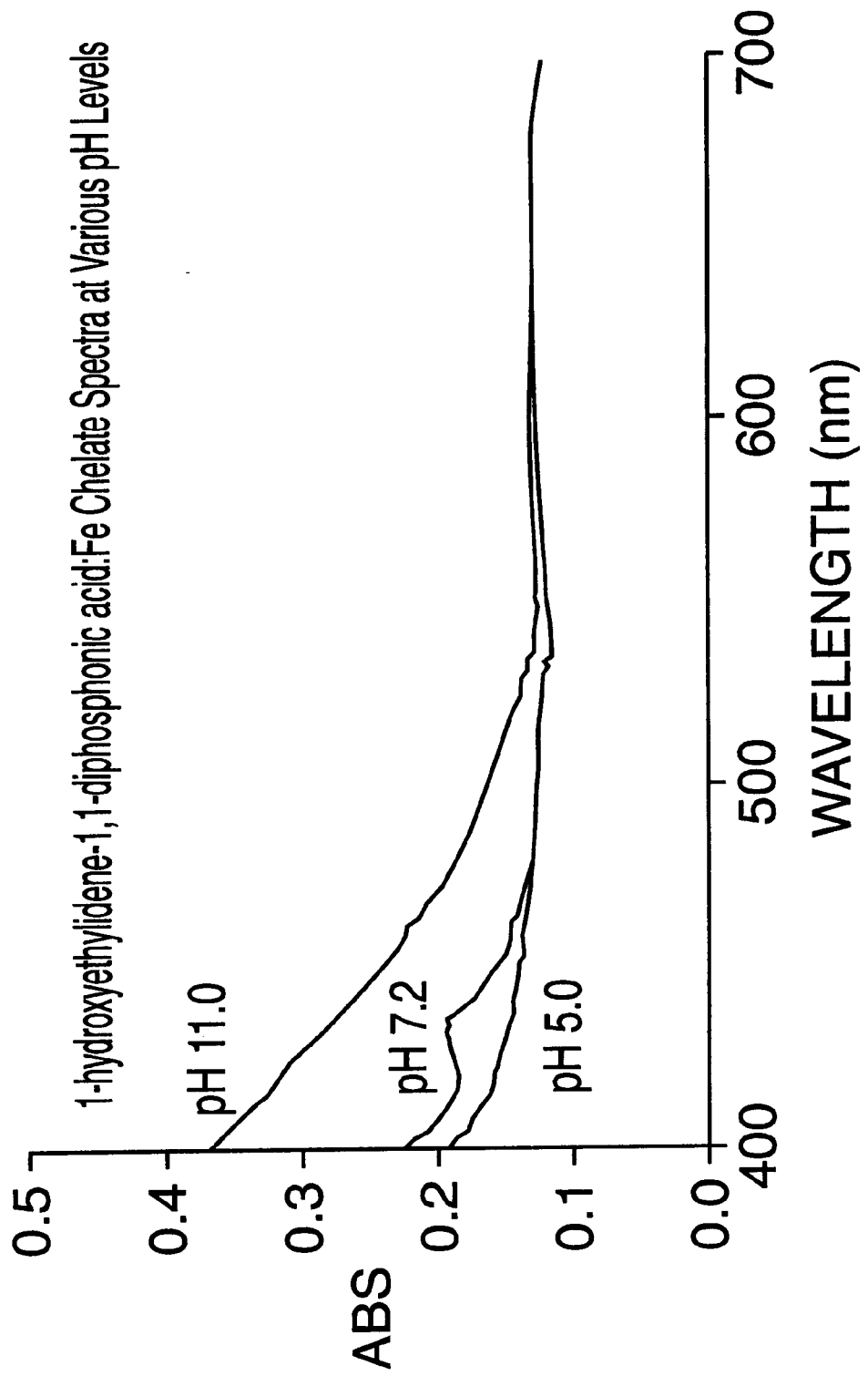
FIG. 3: Graph of Comparative Spectra

Although FIGS. 1 and 2 illustrate embodiments having 3 outputs and 6 outputs, respectively, it is contemplated that the device may have any number of outputs or emitters, from one to a high multiple of outputs. Each output consisting of an individual fiber or fiber bundle that ultimately is connected to a light source. Embodiments having 3 or 6 outputs are presently preferred for the device because they achieve fairly uniform illumination of the eight or more central teeth without excessive manufacturing problems or costs. More than six output, of course are feasible and may in fact be beneficial in terms of uniformity of illumination.

The front surfaces of the device are positioned to give an output configuration such that the combined beams from each optical output converge to illuminate at least the eight central teeth in both the upper and lower arches or the area from the incisors to the first pre-molars in each half arch, a total area of about 10.4 cm$^2$ in the average male. Although depicted in FIG. 1 as linear in form, these outputs may be of any shape, e.g., circular, triangular or linear. Linear forms are preferred. The preferred embodiments have six linear outputs, each output having a length to width ratio of about 16±20%—i.e., ratios of 12.8 to 19.2. In the most preferred embodiment, 80% of the light projected from the outputs onto the 8 upper and lower central teeth is within an area between about 0.9 and about 1.5 inches wide, the approximate distance from the top of the enamel of the top teeth to the bottom of the enamel of the bottom teeth. Each optical output preferably is connected to a distal light source by two glass or plastic fiber optic bundles which originate at the distal light source, enter the device through a socket 20 and terminate at the trifurcated linear output window. Non-uniformity in fiber transmission is generally observed to be minor in the absence of actually breaks in the fibers. Variation in optical output from point to point at the surface of each output or emitter should be no more than about ±10%.

Whether illumination of the stained teeth is performed individually or as a whole, the light emerging from a direct or indirect source may be continuous ("on" the entire procedure), interrupted continuous (primary "on" with short rest interruptions), pulsed ("on" and "off" in a predetermined timed sequence and intensity), or a combination of continuous, interrupted continuous and pulse. In a preferred embodiment from about 10 to about 200 milliWatt/cm$^2$ of light is applied continuously to the front surface of the teeth for a total period of time from about 10 to about 90 minutes. In a more preferred embodiment from about 100 to about 160 milliWatt/cm$^2$ of light is applied continuously or continuously with short interruptions to the front surface of the teeth for a period of time from about 10 minutes to about 30 minutes followed by an interruption or "off" period of about 1 to 10 minutes, with the cycle repeated for a total time of approximately 40–60 minutes. In one envisioned embodiment of the invention a feed-back mechanism based on reflectance would be used to monitor bleaching efficiency and regulate the total amount of actinic radiation applied. In all embodiments of the invention the positioning of the light source affects the energy density applied to the teeth as power density decreases with distance. The preferred placement of the light source will vary depending on the precise nature of the device. For the device described above, the preferred distance for placement of the device is from directly in front of the surface of the teeth up to about 2.0" in front of the surface of the teeth (when measured from the middle of the light source to the central tooth), with a distance of about 1.75" being most preferred.

A number of different sources of actinic radiation have been shown to have utility in the practice of the present invention. In general, any light source capable of emitting actinic radiation in the wavelength range necessary to activate either the inventive photosensitizer(s) or otherwise raise the energy state of tooth chromogens, is contemplated to have utility in the practice of this invention. In particular, light sources capable of emitting actinic radiation that is both biologically safe and effective are preferred, especially those sources which emit limited amounts of infrared light (700 nm and above). Infrared light more readily penetrates the tooth structure and may cause an excessive temperature rise in pulpal tissue. It is preferred that light sources (combined with filters) emitting only those wavelengths necessary for the activation of the inventive photosensitizer and/or the activation of a tooth stain chromophores be used in the process of whitening teeth with the inventive compositions. It is generally accepted that a pulpal temperature rise of more than 5.5° C. for a significant period of time can be irreversibly damaging to the tooth structure.

More specifically, light sources which emit actinic radiation in the wavelength range from about 350 nanometers to about 700 nanometers are especially preferred, in that both the photosensitizers described herein and the tooth chromogen molecules responsible for tooth staining absorb primarily in this region of the spectrum. Light sources which emit actinic radiation in the wavelength ranges from about 400 and about 505 nanometers are most preferred. Output uniformity should be about +/−10% over the area of the beam once transmitted through a glass or plastic fiber to the optical output which may be placed in front of a patient's teeth. Although there are no limitations on the input and length dimensions of such a fiber, one of about 10 millimeters in diameter and 3 meters in length is preferred. Such energy may be provided by a source which generates a continuous electromagnetic spectrum filtered to the preferred wavelengths with a variation of no more than about +/−10%, or by a source which generates an emission line spectrum, or a combination of both. Suitable lamps which emit actinic radiation in the preferred range of wavelengths include linear flash lamps, tungsten halogen, metal halide, Xenon short arc, Mercury short arc, Mercury Xenon short arc, Argon plasma arc, and Argon short arc lamps, among others. The output of two Mejiro BMH 250 watt metal halide lamps filtered through dichroic filters to between about 400 and 505 nanometers meet these criteria.

The following examples set forth preferred embodiments of the invention. These embodiments are merely illustrative and are not intended to, and should not be construed to, limit the claimed invention in any way.

EXAMPLE I

In order to determine the ability of the inventive compositions to eliminate tooth stain, a preliminary in vitro study on stained bovine enamel was performed. Squares of dental enamel 4 mm on a side were cut, using a diamond-cutting disk, from bovine permanent incisors. Using a mold, the enamel squares were embedded in clear polyester casting resin (NATCOL Crafts Inc., Redlands, Calif.) to provide 1.5 cm square blocks with the labial surface exposed. The top surface of the polyester blocks was ground flush with the leveled labial surface of the enamel squares by means of a dental model trimmer. The surface was then smoothed by hand sanding on 400-grit emery paper using water as the lubricant until all grinding marks were removed. Finally, the top surface of the blocks was hand polished to a mirror finish using a water slurry of GK1072 calcined kaolin (median particle size=1.2 microns) on a cotton cloth. The finished specimens were examined under a dissecting microscope and were discarded if they had surface imperfections.

In preparation for the formation of artificial stained pellicle on the enamel, the specimens were etched for 60 seconds in 0.2M HCl followed by a 30-second immersion in a saturated solution of sodium carbonate. A final etch was performed with 1% phytic acid for 60 seconds, then the specimens were rinsed with deionized water and attached to the staining apparatus.

The pellicle staining apparatus was constructed to provide alternate immersion into the staining broth and air-drying of the specimens. The apparatus consisted of an aluminum platform base which supported a Teflon rod (¾ inch in diameter) connected to an electric motor, which by means of a speed reduction box, rotated the rod at a constant rate of 1.5 rpm. Threaded screw holes were spaced at regular intervals along the length of the rod. The tooth specimens were attached to the rod by first gluing the head of a plastic screw to the back of a specimen. The screw is then tightened within a screw hole in the rod. Beneath the rod was a removable, 300-ml capacity trough, which held the pellicle, staining broth.

The pellicle staining broth was prepared by adding 1.02 grams of instant coffee, 1.02 grams of instant tea, and 0.75 grams of gastric mucin (Nutritional Biochemicals Corp., Cleveland Ohio 44128) to 250 ml of sterilized trypticase soy broth. Approximately 50 ml of a 24-hour *Micrococcus luteus* culture was also added to the stain broth. The apparatus, with the enamel specimens attached and the staining broth in the trough was then placed in an incubator at 370 C. with the specimens rotating continuously through the staining broth and air. The staining broth was replaced once every 24 hours for ten consecutive days. With each broth change the trough and specimens were rinsed and brushed with deionized water to remove any loose deposits. On the eleventh day the staining broth as modified by the addition of 0.03 grams of $FeCl_3.6H_2O$, and this was continued with daily broth changes until the stained pellicle film on the specimens was sufficiently dark. Then the specimens were removed from the staining broth, brushed thoroughly with deionized water, and refrigerated in a humidor until used.

Absorbance measurements over the entire visible spectrum were obtained using the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978). The CIELAB color scale evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

The stained enamel specimens were allowed to air-dry at room temperature for at least one hour before absorbance measurements were made. Measurements were conducted by aligning the center of a 4-mm square segment of stained enamel directly over the 3-mm aperture of the Minolta spectrophotometer. An average of 3 absorbance readings using the L*a*b* factors were taken for each specimen.

The difference between the pre-treatment (baseline) and post-treatment readings for each color factor (L*, a*, and b*) represented the ability of a test solution to eliminate chromogens from the stained teeth.

The overall change in color of stained pellicle was calculated using the CIELAB equation $$\Delta E = [(\Delta L^*)^2 + (\Delta a^*)^2 + (\Delta b^*)^2]^{1/2}$$

A "Corrected ΔE" value was calculated by eliminating from the above formulation the contribution of any positive Δa or Δb values (positive Δa and Δb values are changes in tooth color in the opposite direction from zero, and hence construed to add color, rather than remove it).

The following oxidizing composition was prepared, which contained approximately 15% by weight hydrogen peroxide and 1 percent by weight of the photosensitizer precursor 1-hydroxyethylidene-1,1-diphosphonic acid (Dequest 2010, Monsanto Corp., St. Louis, Mo.). Highly purified water (18.2 megaohm, filtered through a 0.2 micron filter) was utilized in order to maintain good stability of the composition during storage. The composition was thickened with a carboxypolymethylene polymer (Carbopol 974P, B.F. Goodrich Co., Cleveland, Ohio) to the consistency of a light, non-runny gel. Glycerin was added in a small percentage as a humectant and stabilizer (as a free radical scavenger), and the Carbopol 974P was neutralized to a pH of 5.00 with ammonium hydroxide, resulting in the formation of a transparent and thixotropic gel.

| Ingredient | Percentage |
| --- | --- |
| Distilled water | 49.400 |
| 1-hydroxyethylidene-1,1-diphosphonic acid | 1.000 |
| Glycerin 99.7% | 5.000 |
| Hydrogen peroxide 35% | 42.900 |
| Carbopol 974P | 1.700 |
| Ammonium hydroxide 29% | to pH 5.5 |
| TOTAL | 100.000 |

The above composition was prepared in a plastic mixing chamber by combining, under agitation with a Teflon-coated mixing paddle until a clear solution was obtained, the distilled water, the 1-hydroxyethylidene-1,1-diphosphonic acid, and the glycerin. The Carbopol 974P was then sifted slowly into the vortex created by the mixing paddle and allowed to mix until a homogeneous slurry of the polymer was obtained. Finally, the ammonium hydroxide was added in a constant, dropwise fashion over a period of about 5 minutes until thickening and clarification of the slurry occurred. A pH probe was inserted periodically and the ammonium hydroxide addition proceeded until a pH of exactly 5.00 was obtained. The resulting gel contained 15% by weight hydrogen peroxide, and was highly transparent and thixotropic (non-slumping) in character.

Each stained bovine enamel slab was coated with a 1–2 mm film of the composition in Example I above for a specified period of time and exposed to actinic radiation from one of several light sources. Table 1 below shows some comparative results obtained by exposing gel-treated enamel slabs to either Argon plasma arc (AR) or tungsten halogen (TH) light sources. This particular protocol called for the fiber optic light guide to be placed 5 mm from the surface of the enamel during light exposures. The energy of each pulse was adjusted with a power density meter prior to each exposure regimen and measured again after each regimen to verify consistent output of the light source over the duration of the test. The results are listed in Table 1 below:

TABLE 1

| Bovine Tooth # | Light Source | Total Gel Contact Time | Number of Pulses | Energy/Pulse (Joules) | Corrected Delta E* |
|---|---|---|---|---|---|
| B311 | None | 30 min | 0 | 0.00 | 12.76 |
| B388 | AR | None | 30 | 1.66 | 1.41 |
| B277 | AR | 30 min | 30 | 1.66 | 29.28 |
| B214 | AR | 30 min | 30 | 3.35 | 29.75 |
| B283 | AR | 10 min | 10 | 3.29 | 18.62 |
| B147 | AR | 10 min | 10 | 4.90 | 25.98 |
| B401 | AR | 10 min | 30 | 4.97 | 32.18 |
| B211 | AR | 5 min | 15 | 4.84 | 20.05 |
| B213 | AR | 5 min | 30 | 4.93 | 31.02 |
| B35 | TH | 5 min | 15 | 1.29 | 12.88 |
| B35 | TH | 5 min | 15 | 1.29 | 19.39 |
| B35 | TH | 5 min | 15 | 1.29 | 20.01 |
| B35 | TH | 5 min | 15 | 1.29 | 23.61 |
| B35 | TH | 5 min | 15 | 1.29 | 25.35 |
| B35 | TH | 5 min | 15 | 1.29 | 26.41 |

*Elimination of positive Δa and Δb values from calculation

The data in Table 1 demonstrates that:

(1) In the in vitro model described, exposure of bovine enamel slabs, contacted with the inventive gel composition above, to pulsed actinic radiation from a Argon plasma arc light source resulted in significantly reduced tooth stain as compared to slabs treated either with just gel alone (and not exposed to the light source) or light source exposure only (no gel).

(2) Six sequential treatments (over 30 minutes) of a single stained bovine enamel slab (B35) with gel and concurrent exposure of said slab to pulsed actinic radiation from a tungsten halogen light source (5 minute exposure periods) resulted in an increasing level of tooth stain removal over the period of the test. The result was significantly lighter in color than that achieved in tooth number B311, which was also in contact with the inventive gel composition, but did not get exposed to a light source.

EXAMPLE II

Figure 4A:
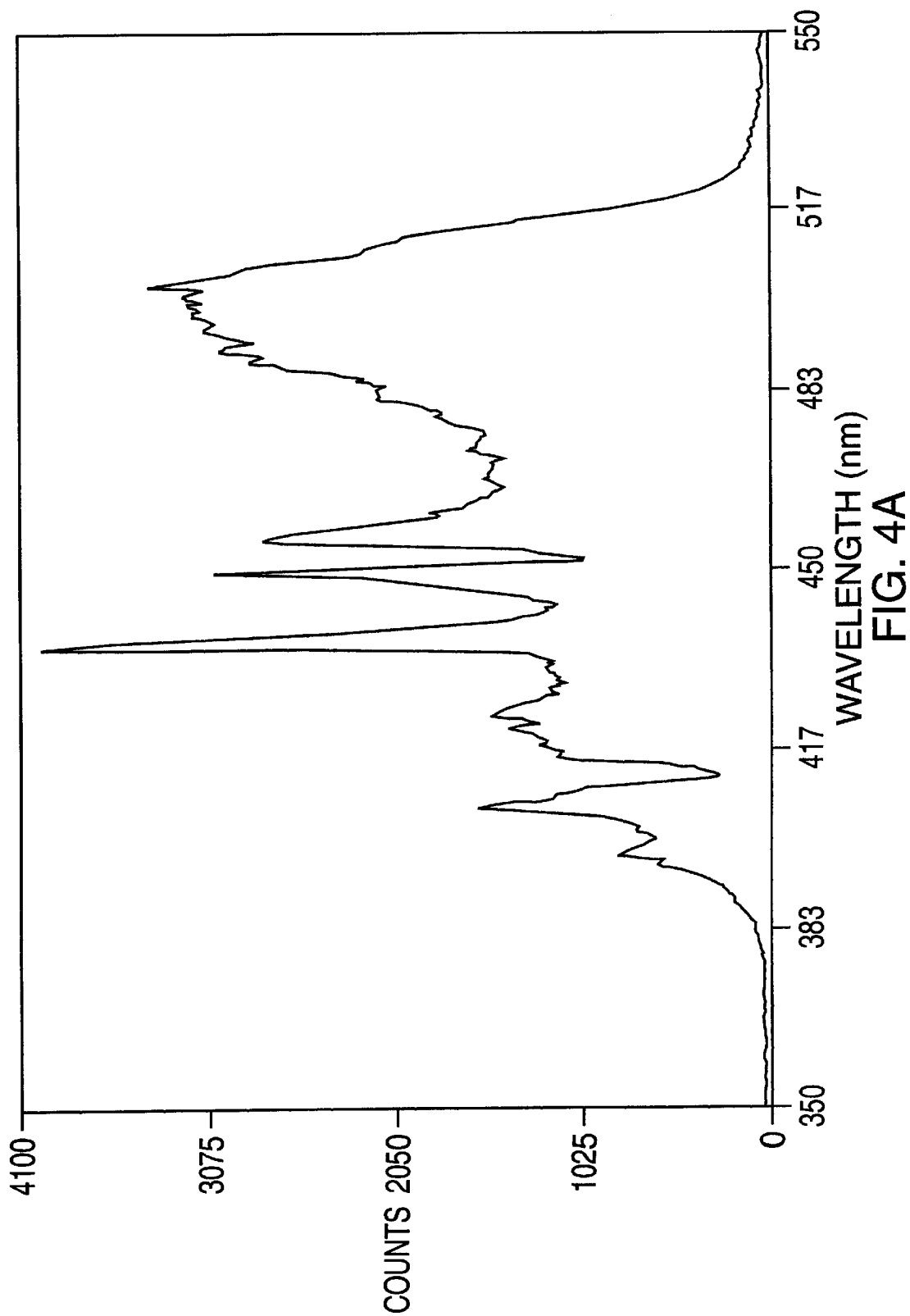
FIG. 4: Spectral Curves of Light Attenuation
Figure 4B:
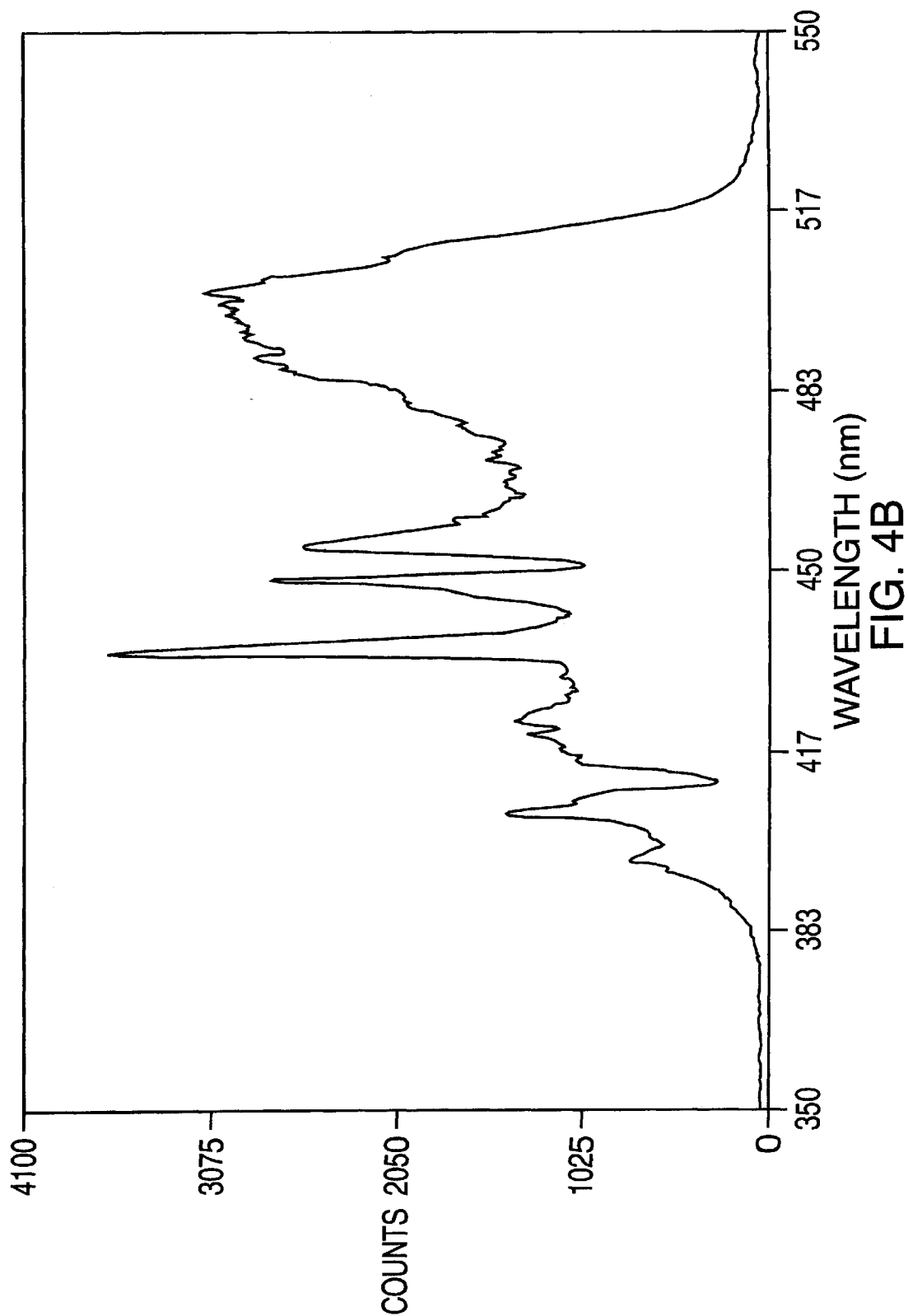
Figure 4D:
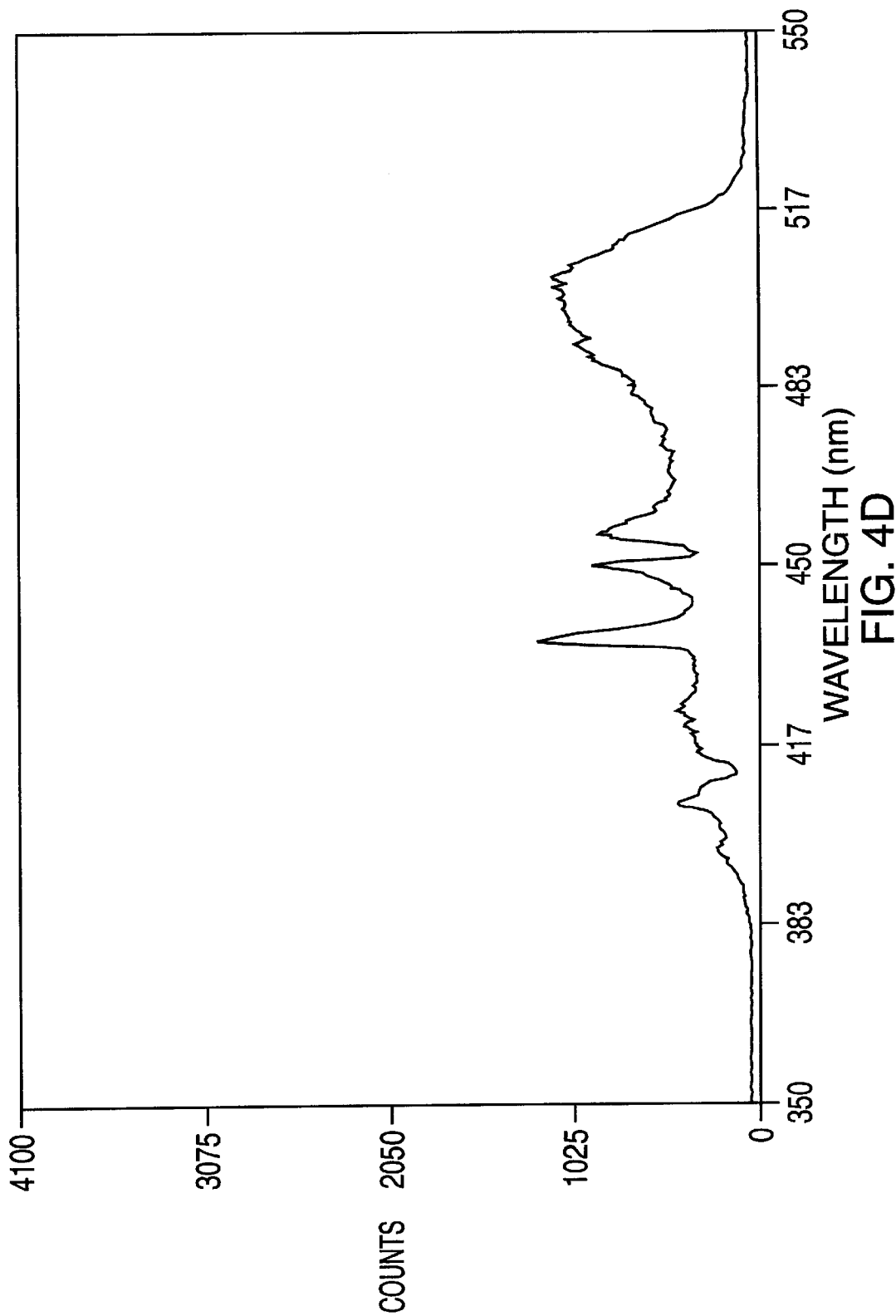
Figure 4E:
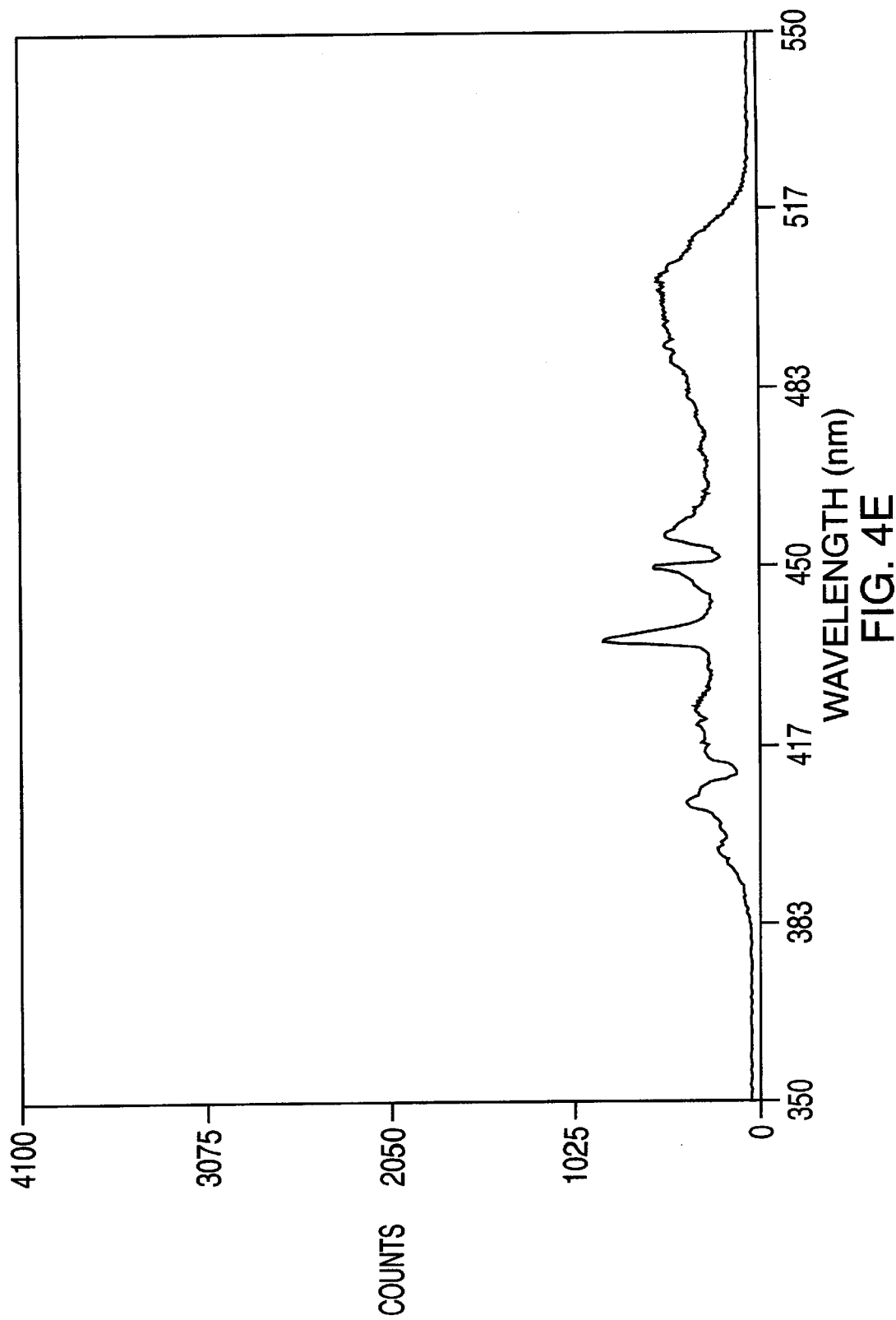

A comparative study of light transmission through various light and/or heat activated tooth whitening gels was undertaken. Spectral energy curves were generated using an Ocean Optics spectrometer with a 50 micron fiber for gather emission data. Light transmission through a glass microscope slide was used as a control and the test consisted of coating the slide with a 1–2 mm thick layer of each tooth whitening gel and illuminating with a metal halide light source connected to an 8 mm glass fiber optic light guide. The light was filtered through a 505 nm short pass filter (only wavelengths less than 505 nm pass through) prior to entering the light guide. The spectrometer's fiber optic probe was placed against the opposite side of the slide from the gel in order to detect the wavelengths of light allowed to pass through the gel on the slide. The spectral curves of FIGS. 4A–E clearly demonstrate the degree of light attenuation caused by all of the commercially available compositions: FIG. 4A—Control; FIG. 4B—Inventive Example I; FIG. 4C—Shofu Hi-Lite; FIG. 4D—QuasarBrite; FIG. E—Opalescence Xtra.

The attenuation of power density, measured in mW/cm$^2$, was determined for the same four compositions by again placing a 1–2 mm layer of each gel or paste on a glass microscope slide and placing the slide/gel assembly in the path between the light source and the detector well of the power density meter. Due to the depth and shape of the detector well, the slide was 7 mm above the actual detector surface, rather than directly in contact with it. The power density was recorded at the beginning (B) and at the end of a 60 minute light exposure (E). The power density without slide or gel in the light path was adjusted to 175 mW/cm$^2$. The results are shown in Table 2 below.

TABLE 2

| Composition | U.S. Pat. No. | Energy Density (m W/cm$^2$) |
|---|---|---|
| Control (slide only) | — | 165 |
| Example I (B) + (E) | — | 160 |
| & So Shofu Hi-Lite (B) | 5,032,178 | 25 |
| Shofu Hi-Lite (E) | 5,032,178 | 50 |
| QuasarBrite (B) | 5,240,415 | 110 |
| QuasarBrite (E) | 5,249,415 | 111 |
| Opalescence Xtra (B) | 5,785,527 | 65 |
| Opalescence Xtra (E) | 5,785,527 | 94 |

EXAMPLE III

Another transparent hydrogen peroxide gel was prepared that had a lower concentration of oxidizer (3% by weight of $H_2O_2$), but at a pH of 7.0 and a much higher viscosity (approximately 1,000,000 cps). The gel below was prepared in accordance with the procedure in Example I, except that a Kynar coated Ross Double Planetary vacuum mixer (Charles Ross & Sons, Haupaugge, N.Y.) was used to handle the elevated viscosity achieved during and after neutralization with the ammonium hydroxide. Sodium stannate was added as an additional stabilizer for the hydrogen peroxide.

| Ingredient | Percentage |
|---|---|
| Distilled water | 81.010 |
| Glycerin 99.7% | 5.000 |
| 1-hydroxyethylidene-1,1-diphosphonic acid | 0.400 |
| Sodium stannate | 0.015 |
| Hydrogen peroxide 35% | 8.570 |
| Carbopol 974P | 5.000 |
| Ammonium hydroxide 29% | to pH 7.0 |
| TOTAL | 100.000 |

The ability of the 3% hydrogen peroxide gel, transparent to visible light between the wavelengths of 380 and 700 nanometers, is demonstrated in Table 3 below.

TABLE 3

| Bovine Tooth # | Oxidizing Gel | Time Period | Light Source | Wavelength Range (nanometers) | Pulses/ Period | Power Density (mW/cm2) | Energy/ Pulse (Joules) | Delta E* |
|---|---|---|---|---|---|---|---|---|
| B388 | Example II | 5 min | AR | 380–505 | 15 | | 4.84 | 19.67 |
| B388 | Example II | 5 min | AR | 380–505 | 15 | | 4.84 | 29.43 |

TABLE 3-continued

| Bovine Tooth # | Oxidizing Gel | Time Period | Light Source | Wavelength Range (nanometers) | Pulses/ Period | Power Density (mW/cm2) | Energy/ Pulse (Joules) | Delta E* |
|---|---|---|---|---|---|---|---|---|
| B388 | Example II | 5 min | AR | 380–505 | 15 | | 4.84 | 32.74 |
| B365 | Example II | 5 min | None | — | 0 | | 0 | 3.41 |
| B365 | Example II | 5 min | None | — | 0 | | 0 | 4.23 |
| B365 | Example II | 5 min | None | — | 0 | | 0 | 5.78 |
| B365 | Example II | 5 min | AR | 380–505 | 15 | | 4.84 | 23.49 |
| B365 | Example II | 5 min | AR | 380–505 | 15 | | 4.84 | 30.27 |
| B367 | Example I | 30 min | TH | 400–520 | Continuous | 250 | | 32.26 |

* Elimination of positive Δa and Δb values from calculation.

EXAMPLE IV

Extracted human teeth (HE) that were non-carious and free of amalgam or resin-based restorative materials were utilized to study the ability of the inventive compositions to eliminate the stains from human enamel and dentin. The teeth were coated with a 1–2 mm thick film of an oxidizing gel and irradiated according to the regimens shown in Table IV below. The resulting change in tooth color (Δ Shades) was recorded as the number of VITA® shade difference between the original baseline VITA® shade value and the final VITA® shade value.

EXAMPLE V

Human extracted teeth were whitened as follows by applying a 1–2 mm thick film of gel on the enamel surface and exposing the same surface to varying power densities from a metal halide light source with a 505 nm short pass internal filter. Comparisons were done to two controls, one of which was Gel exposure only (no light) and light exposure only (no Gel). Exposure regimens, consisting of gel application (except in the case of light only/no Gel), followed by 20 minutes of continuous light exposure, were repeated three times (3×20 minutes).

TABLE 4

| Tooth # | Gel | Light Source | Exposure Time (min) | Pulses/ Minute | Joules/ Pulse | Shade (Initial) | Shade (Final) | Δ Shade |
|---|---|---|---|---|---|---|---|---|
| HE2 | Example I | AR | 30 | 1 | 4.84 | B4 | C2 | 6 |
| HE3 | Example I | AR | 30 | 1 | 4.84 | A4 | A3.5 | 3 |
| HE4 | Example I | AR | 30 | 1 | 4.84 | A3 | B2 | 6 |
| HE5 | Example I | AR | 30 | 1 | 4.84 | B3 | D4 | 3 |
| HE6 | Example I | AR | 30 | 1 | 4.84 | B3 | B2 | 8 |
| HE7 | Example I | AR | 30 | 1 | 4.84 | A3 | A1 | 7 |
| HE8 | Example I | AR | 30 | 1 | 4.84 | A3.5 | A2 | 7 |
| HE9 | Example I | AR | 30 | 1 | 4.84 | A3 | A1 | 7 |
| HE10 | Example I | AR | 30 | 1 | 4.84 | A4 | A3.5 | 6 |
| HE11 | Example I | AR | 30 | 1 | 4.84 | A3.5 | A2 | 7 |
| HE12 | Example I | AR | 30 | 2 | 4.84 | A3.5 | A2 | 7 |
| HE13 | Example I | AR | 30 | 2 | 4.84 | B3 | B2 | 8 |
| HE14 | Example I | AR | 30 | 2 | 4.84 | A3.5 | B2 | 9 |
| HE15 | Example I | AR | 30 | 2 | 4.84 | A4 | A1 | 13 |
| HE16 | Example I | AR | 30 | 2 | 4.84 | B4 | B1 | 12 |
| HE17 | Example I | AR | 30 | 1 | 1.64 | A3 | A2 | 4 |
| HE18 | Example I | AR | 30 | 1 | 1.64 | B4 | B2 | 10 |
| HE19 | Example I | AR | 30 | 1 | 1.64 | C4 | D3 | 6 |
| HE20 | Example I | AR | 30 | 1 | 1.64 | B3 | A2 | 6 |
| HE21 | Example I | AR | 30 | 1 | 1.64 | B3 | B2 | 8 |
| HE22 | Example I | No light | 30 | 0 | 0 | B3 | A2 | 2 |
| HE23 | Example I | No light | 30 | 0 | 0 | A3 | A2 | 4 |
| HE24 | Example I | No light | 30 | 0 | 0 | B3 | D4 | 3 |
| HE25 | Example I | No light | 30 | 0 | 0 | D3 | B2 | 7 |
| HE26 | Example I | No light | 30 | 0 | 0 | B3 | A2 | 6 |
| HE27 | Example I | Tungsten Halogen | 60 | Continuous | 250 mW/cm2 | B3 | A1 | 9 |

TABLE 5

| Tooth # | Gel | Light Source | Power Density (mW/cm2) | Filter | Test Duration | Initial Shade | Final Shade | Shade Change |
|---|---|---|---|---|---|---|---|---|
| HE101 | Example I | MH | 250 | 505 | 3 × 20 min | A3.5 | A1 | 7 |
| HE102 | Example I | MH | 250 | 505 | 3 × 20 min | B4 | A2 | 8 |
| HE103 | Example I | MH | 175 | 505 | 3 × 20 min | A3 | B1+ | 8 |
| HE104 | Example I | MH | 175 | 505 | 3 × 20 min | A4 | B2 | 12 |
| HE105 | Example I | MH | 175 | 505 | 3 × 20 min | B3 | B2 | 8 |
| HE106 | Example I | MH | 175 | 505 | 3 × 20 min | A3 | B1+ | 8 |
| HE107 | Example I | MH | 175 | 505 | 3 × 20 min | A4 | A2 | 10 |
| HE108 | Example I | No light | | | 3 × 20 min | A3.5 | A3 | 3 |
| HE109 | Example I | No light | | | 3 × 20 min | A4 | D3 | 5 |
| HE110 | Example I | No light | | | 3 × 20 min | A3.5 | A3.5 | 0 |
| HE111 | Example I | No light | | | 3 × 20 min | A4 | A3 | 6 |
| HE112 | Example I | No light | | | 3 × 20 min | A4 | A3.5 | 3 |
| HE113 | None | MH | 175 | 505 | 3 × 20 min | A3 | A3 | 0 |
| HE114 | None | MH | 175 | 505 | 3 × 20 min | A4 | A4 | 0 |
| HE115 | None | MH | 175 | 505 | 3 × 20 min | A3.5 | A3 | 3 |
| HE116 | None | MH | 175 | 505 | 3 × 20 min | B3 | B3 | 0 |

EXAMPLE VI

A pulpal chamber of an endo-tooth in a cooperative and informed patient was wired using a thermal probe and thermo-conducting paste. Pulpal temperatures were measuring during an actual whitening procedure, in which the illumination was supplied using the currently available Union Broach Illuminator and the device described in the instant application used at the most preferred wavelengths of 400 to 505 nanometers. Measurements of the energy densities at the tooth surface showed comparable energy densities for each device (230 milliwatts/cm$^2$ for the Union Broach Illuminator and 200 milliwatts/cm$^2$ for the device described in the instant application, respectively). The results are shown below in Table 6.

Illumination using the device described in the instant application in the preferred wavelength range from about 400 to 505 nanometers raised pulpal chamber temperature less than did the Union Broach device. In this experiment, temperatures rose to a maximum by twenty minutes and were then stable. In contrast to the temperature rise seen with the Union Broach device, at no time did the temperature using the device disclosed in the instant application rise above the 5.5° C. which could result in thermally induced pulpitis if maintained for a significant period of time. The temperature changes seen are likely to be greater than those seen with vital teeth as endo-teeth have no blood supply to provide additional cooling.

| Time (min.) | Temperature Rise (deg. C. from ambient) | |
|---|---|---|
| | Union Broach | BriteSmile 2000 |
| 5 | 4 | 2.9 |
| 10 | 8 | 4.5 |
| 15 | 9 | 5.3 |
| 20 | 9 | 4.2 |
| 25 | 9.5 | 4.5 |
| 30 | 9 | 4.3 |

Upon reading the subject application, various alternative constructions and embodiments will become obvious to those skilled in the art. These variations are to be considered within the scope and spirit of the subject invention. The subject invention is only to be limited by the claims which follow and their equivalents.

What is claimed:

1. A method for light-activated tooth whitening comprising the steps of:
   applying a photosensitizing agent which absorbs actinic radiation when in contact with the surface of a tooth to one or more teeth;
   applying an tooth-whitening composition containing a transparent carrier compound and a transparent oxidizing compound capable of facilitating tooth whitening on top of said photosensitizing agent; and
   exposing said photosensitizing agent and said tooth-whitening composition to actinic light to activate said oxidizing compound.

2. A method as set forth in claim 1 wherein said photosensitizing agent absorbs light having a range of wavelengths from about 350 nanometers to about 700 nanometers and converts that energy into thermal or chemical energy.

3. A method as set forth in claim 2 wherein said photosensitizing agent absorbs light having a range of wavelengths from about 380 nanometers to about 500 nanometers.

4. A method as set forth in claim 1 wherein said photosensitizing agent is of molecular size, pH and surface charge to allow for effective penetration into the structure of the enamel and dentin.

5. A method as set forth in claim 1 wherein said photosensitizing agent is selected from a group consisting of nanometer sized semiconductor particles, benzophenone derivatives, benzotriazole derivatives, diketones, metal-ligand complexes, and phthalocyancin-metal complexes.

6. A method as set forth in claim 1 wherein said light source emits light having a range from about 350 nanometers to about 700 nanometers.

7. A method as set forth in claim 6 wherein said light source emits light having a range from about 380 nanometers to about 500 nanometers.

8. A method as set forth in claim 1, wherein the transparent oxidizing compound is selected from the group consisting of peroxides, peroxyacids and combinations thereof.

9. A method as set forth in claim 8, wherein the transparent oxidizing compound is a peroxide.

10. A method as set forth in claim 9, wherein the peroxide is hydrogen peroxide.

11. A method as set forth in claim 8, wherein the transparent oxidizing compound is a peroxyacid.

12. A method as set forth in claim 11, wherein the peroxyacid is peroxyacetic acid.

* * * * *

UNITED STATES PATENT AND TRADEMARK OFFICE
CERTIFICATE OF CORRECTION

PATENT NO. : 6,162,055
DATED : December 19, 2000
INVENTOR(S) : Montgomery et al.

It is certified that error appears in the above-identified patent and that said Letters Patent is hereby corrected as shown below:

Title page,
Column 1,
Line 1, please replace "LIGHT ACTIVATED" with -- LIGHT-ACTIVATED --.
Line 6, after Ser., please replace "No." with -- Nos. --.
Lines 6-7, please delete "Ser. No.".

Column 7,
Line 12, after heat "of" should read -- or --.

Column 13,
Line 27, after 370 please insert -- o --.

Column 16,
Line 37, replace "Haupaugge" with -- Hauppauge --

Claim 1,
Line 28, after applying, please delete "an" and replace it with -- a --.

Signed and Sealed this

Thirtieth Day of October, 2001

Attest:

NICHOLAS P. GODICI
Attesting Officer      Acting Director of the United States Patent and Trademark Office

UNITED STATES PATENT AND TRADEMARK OFFICE
CERTIFICATE OF CORRECTION

PATENT NO. : 6,162,055  
DATED : December 19, 2000  
INVENTOR(S) : Montgomery et al.

Page 1 of 1

It is certified that error appears in the above-identified patent and that said Letters Patent is hereby corrected as shown below:

<u>Column 13,</u>  
Line 27, delete "370 C" and replace with -- thirty-seven degrees Centigrade --

Signed and Sealed this

Nineteenth Day of February, 2002

Attest:

JAMES E. ROGAN  
*Director of the United States Patent and Trademark Office*

*Attesting Officer*